United States Patent [19]
Hase et al.

[11] Patent Number: 5,516,701
[45] Date of Patent: May 14, 1996

[54] METHOD FOR TRACE ANALYSIS OF IMPURITY, AND LIGHT ABSORPTION MEASURING APPARATUS, MEASURING CELL AND ALIQUOTTING DEVICE USED IN THE METHOD

[75] Inventors: Ushio Hase, Tokyo; Kazuhisa Yoshimura, Fukuoka, both of Japan

[73] Assignee: NEC Corporation, Tokyo, Japan

[21] Appl. No.: 486,231

[22] Filed: Jun. 7, 1995

Related U.S. Application Data

[63] Continuation of Ser. No. 59,354, May 11, 1993, abandoned.

[30] Foreign Application Priority Data

May 11, 1992 [JP] Japan ................................. 4-116583

[51] Int. Cl.$^6$ ................................................. G01N 21/75
[52] U.S. Cl. ........................... 436/164; 436/166; 436/178; 436/100; 436/174; 422/82.05
[58] Field of Search ....................... 436/100, 164, 436/166, 178, 52, 56, 73, 80, 81, 168, 174; 422/82.03, 82.05

[56] References Cited

U.S. PATENT DOCUMENTS

| | | | |
|---|---|---|---|
| 3,811,837 | 5/1974 | Hoffman | 436/100 X |
| 3,920,397 | 11/1975 | Small et al. | 436/100 X |
| 4,009,004 | 2/1977 | Hutchinson | 436/105 |
| 4,314,823 | 2/1982 | Rich | 436/100 |
| 4,544,639 | 10/1985 | Faust | 436/104 |
| 5,149,502 | 9/1992 | Dablainville et al. | 422/62 |
| 5,270,216 | 12/1993 | Kan et al. | 436/103 |

OTHER PUBLICATIONS

Yoshimura et al., "Ion–Exchanger Phase Absorptiometry for Trace Analysis", Talanta, 1985, vol. 32, No. 5, pp. 345–352.
Yoshimura et al., "Microdetermination of Silicic Acid in Water by Gel–Phase Colorimetry with Molybdenum Blue", Analytical Chemistry 1984, 56, pp. 2342–2345.
U. Hase et al., "Determination of Silicic Acid in Highly Purified Water by Improved Gel–Phase Absorptiometry", Analytical Sciences, Feb. 1993, 9, pp. 111–115.

*Primary Examiner*—James C. Housel
*Assistant Examiner*—Harold Y. Pyon
*Attorney, Agent, or Firm*—Sughrue, Mion, Zinn, Macpeak & Seas

[57] ABSTRACT

In an analytical method for trace amounts of silicic acid in pure water of the present invention, swollen gel which has been swollen with pure water sufficiently is used as granular solid which adsorbs colored silicic acid species. A small amount of swollen gel is aliquotted volumetrically, and then the gel is added to a sample solution. Colored silicic acid species is adsorbed and concentrated on a small amount of the granular solid. Therefore, trace amounts of silicic acid can be determined with high sensitivity.

4 Claims, 5 Drawing Sheets

FIG.1 PRIOR ART

WATER SAMPLE, 100cm$^3$
  │  AMMONIUM
  │  MOLYBDATE, 2cm$^3$
  ▼
STIRRING OF 15min
  │  12M SULFURIC ACID SOLUTION, 10cm$^3$
  │  ASCORBIC ACID, 1cm$^3$
  │  DRY GEL, 0.2g (PRE WEIGHTED)
  ▼
STIRRING OF 20min
  │
  ▼
SEPARATION OF SEDIMENTED GEL
  │
  ▼
MEASURING ABSORBANCE 450nm, 805nm 5,516,701

METHOD FOR TRACE ANALYSIS OF IMPURITY, AND LIGHT ABSORPTION MEASURING APPARATUS, MEASURING CELL AND ALIQUOTTING DEVICE USED IN THE METHOD

This is a Continuation of application Ser. No. 08/059,354 filed May 11, 1993 now abandoned.

FIELD OF THE INVENTION

This invention relates to a method for trace analysis of impurity, and more particularly, to a method for determining trace amounts of impurity using a direct light absorption measurement of solid phase.

BACKGROUND OF THE INVENTION

In a various fields such as electronics industry, it is required that trace amounts of impurity existing in a raw material can be determined. When an analytical method is not sensitive enough for trace amounts of impurity to be determined, the impurity is concentrated by various kinds of preconcentration techniques prior to the determination of the impurity amounts.

In case of an absorptiometry, one of conventional methods to improve a sensitivity is described on page 345 in a report "Talanta", Vol. 32, No. 5, 1985. In this report, granular solid such as ion-exchanger, which is weighed out prior to use, is added to a sample solution, whereby an impurity contained in the sample solution is adsorbed and concentrated on the granular solid. And then, the color of the impurity is developed in the solid.

After separated from the solution, the solid is charged into a filling portion of a measuring cell. Next, a light absorption of the solid phase is measured at definite wavelengths directly. And then, the amounts of impurity are determined by using a calibration graph.

Generally, the smaller amount of granular solid is employed in the analytical method, the higher concentration of a trace impurity is obtained in the solid.

The conventional method for trace analysis of impurity, however, has disadvantages, that is, it is difficult to aliquot a small amount of the solid with high reproducibility due to its hygroscopic property. In particular, an influence of a moisture absorption in aliquotting the solid is pronounced when the weight of the solid used in the analytical method is less than 0.1 g.

Further, when the filling portion capacity of the light absorption measuring cell is much larger than the volume of the solid used, a part of light beam passes through an unpacked area with the solid and directly reaches to a photo detector of a spectrophotometer. As a result, the absorbance obtained is unreliable.

SUMMARY OF THE INVENTION

Accordingly, it is an object of the invention to provide a highly sensitive method for trace analysis of impurity.

It is a further object of the invention to provide measuring cells whereby a light absorption of a small amount of the solid is measured easily with high sensitivity.

It is a still further object of the invention to provide an aliquotting device whereby a definite volume of swollen solid can be aliquotted with high precision.

According to a first feature of the invention, a method for trace analysis of impurity includes the steps: preparing a sample solution containing impurity; volumetrically aliquotting a definite amount of the sufficiently swollen granular solid with the aliquotting device described before; adding the swollen granular solid into the sample solution whereby the impurity is adsorbed and concentrated in the granular solid; developing the color of the impurity in the granular solid; separating the granular solid from the sample solution; and measuring a light absorption of the granular solid directly, whereby the amount of impurity is determined.

According to a second feature of the invention, an apparatus for a direct light absorption measurment of granular solid which adsorbs colored impurity species, comprising: a syringe for collecting the granular solid with an equilibrated solution therein; a flow-through cell having a sample filling portion in which the granular solid is filled; and a joint for connecting the syringe to the flow-through cell; wherein the granular solid filled in the sample filling portion is irradiated with a light beam to measure absorbance of the granular solid at fixed wavelengths directly whereby the amount of impurity is determined.

According to a third feature of the invention, a measuring cell, comprising: a cell body having a sample filling portion in which granular solid adsorbing colored impurity species is filled; and a height adjuster for adjusting a vertical position of the sample filling portion to that of a light beam; wherein the granular solid filled in the sample filling portion is irradiated with the light beam to measure a light absorption of the granular solid directly whereby the amount of impurity is determined.

According to a fourth feature of the invention, a measuring cell, comprising: a cell body having a sample filling portion in which granular solid adsorbing colored impurity species is filled; and means for shading a part of a light beam whereby only the sample filling portion packed with the granular solid is irradiated with the light beam; wherein a light absorption of the granular solid directly is measured at definite wavelengths to determine the impurity amounts.

According to a fifth feature of the invention, an aliquotting device for volumetrically measuring the swollen granular solid therein, comprising: a syringe; a connection tube connected to an end of the syringe; a metering tube having an open end from which the swollen granular solid slurry is sucked; a joint for connecting the connection tube and the other end of the metering tube; and a filter arranged between the metering tube and the joint, through which the granular solid does not pass but water and air pass. With the device, the swollen granular solid is sucked from its slurry into a metering tube and a fixed volume of the swollen granular solid is held in the metering tube, and the fixed volume corresponds to an internal volume of the metering tube.

The other objects and features of the invention will become understood from the following description with reference to the accompanying drawings.

BRIEF DESCRIPTION OF THE DRAWINGS

FIG. 1 is a flow diagram showing steps for trace analysis of impurity by a conventional method;

DESCRIPTION OF PREFERRED EMBODIMENTS

For better understanding the background of the present invention, the basic principle of the technology is first described hereinafter with reference to FIG. 1. FIG. 1 shows steps for trace analysis of silicic acid in pure water according to a conventional method.

In this analytical method, first, 2 cm$^3$ solution composed of 20% (m/v) ammonium molybdate −2.5 mol dm$^{-3}$ sulfuric acid is added to a 100 cm$^3$ ultra pure water sample, and then is stirred for 15 mins. After that, 10 cm$^3$ of 12 mol dm$^{-3}$ sulfuric acid solution, 1 cm$^3$ of 10% (m/v) ascorbic acid solution and 0.2 g of dry gel (weighed out prior to use) are added to the sample solution, and then is stirred for 20 mins. whereby silicic acid (colored species) is adsorbed and concentrated on the gel. The sample solution is allowed to stand whereby the settled gel is obtained, after that the supernatant liquid is removed. Then, the settled gel is sucked by a syringe and is charged into a filling portion of a measuring cell (not shown). The measuring cell having the gel is set in a cell holder of a spectrometer (not shown), and a light absorption of the gel is measured at 805 nm and 450 nm. And then, the amount of silicic acid is determined by using a calibration graph.

As mentioned before, the conventional method for trace analysis of impurity, however, has disadvantages, that is, it is difficult to aliquot a small amount of the solid with high reproducibility due to its hygroscopic property.

Figure 2:
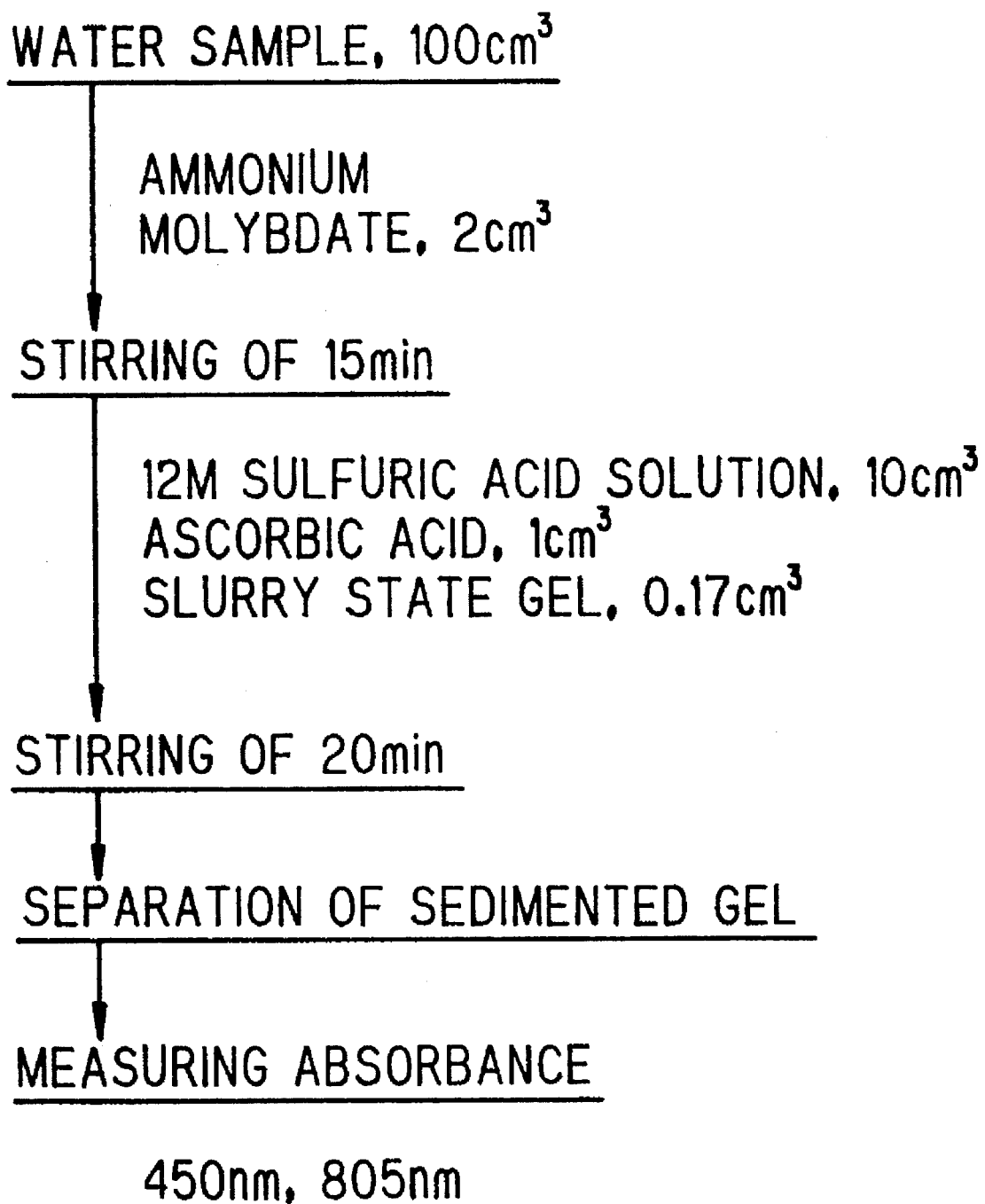
FIG. 2 is a flow diagram showing steps for trace analysis of impurity by a method of a first preferred embodiment according to the invention.

FIG. 2 shows steps for trace analysis of silicic acid in pure water by a method of a first preferred embodiment according to the invention.

In this analytical method, first, 2 cm$^3$ of solution composed of 20% (m/v) ammonium molybdate −2.5 mol dm$^{-3}$ sulfuric acid is added to a 100 cm$^3$ ultra pure water sample, and then is stirred for 15 mins. After that, 10 cm$^3$ of 12 mol dm$^{-3}$ sulfuric acid solution, 1 cm$^3$ of 10% (m/v) ascorbic acid solution and 0.17 cm$^3$ of swollen gel, which has been swollen with pure water sufficiently, are added to the sample solution. At this time, the swollen gel is measured volumetrically with an aliquotting device shown in FIG. 3, which will be explained later.

After that, the sample solution is stirred for 20 mins. whereby silicic acid (colored species) is adsorbed and concentrated on the gel. Then, the sample solution is allowed to stand whereby the gel is settled, after that the supernatant liquid is removed. Next, the settled gel is sucked by a syringe and is charged into a filling portion of a flow-through cell shown in FIG. 4, which will be explained later.

After that, the measuring cell is set in a cell holder of a spectrometer (not shown), and a light absorption of the gel is measured at 805 nm and 450 nm. And then, the amount of silicic acid is determined by using a calibration graph which is obtained by analyzing standards samples by the same method described above.

Figure 3:
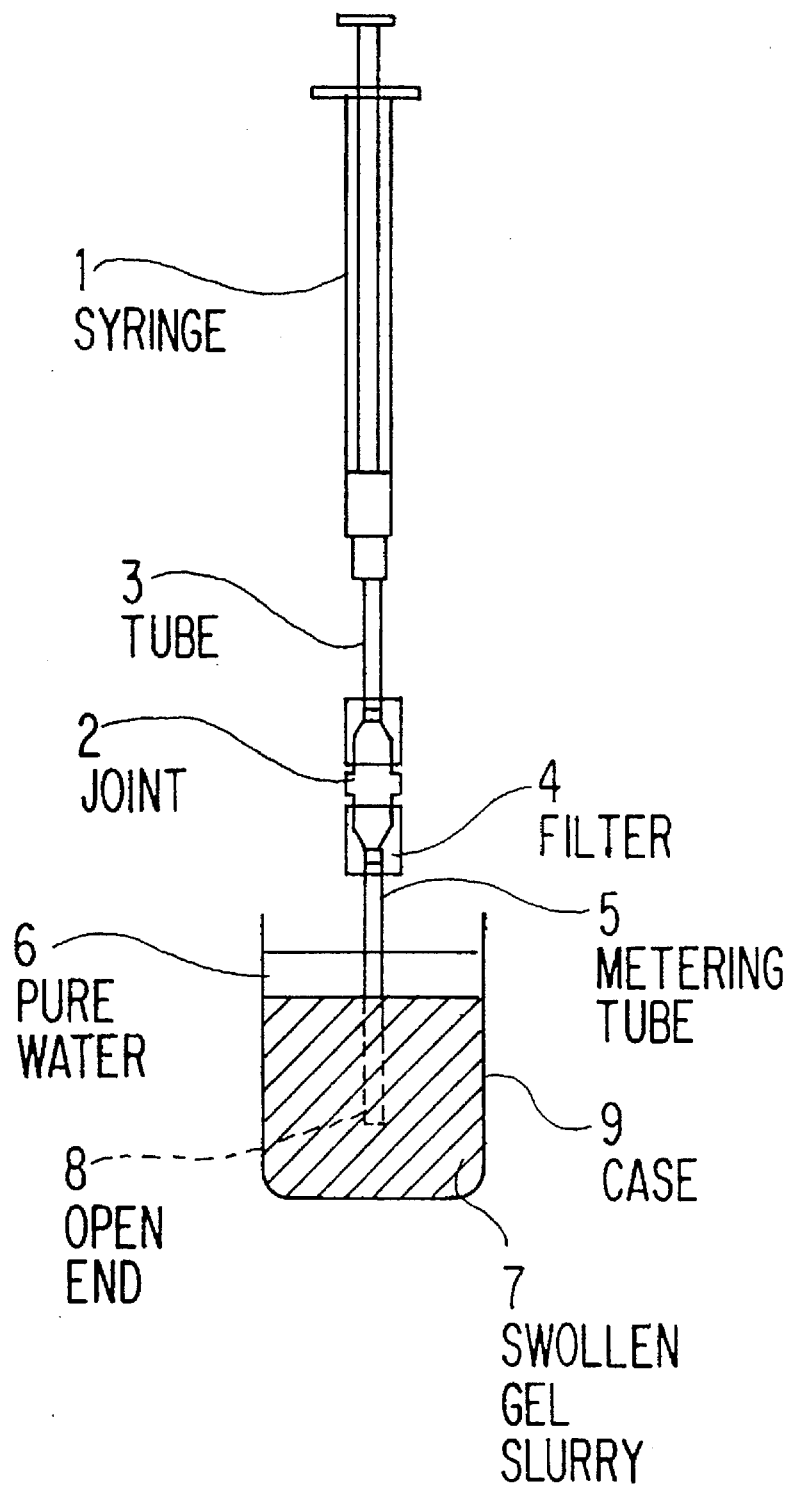
FIG. 3 is a front view showing aliquotting device used in the first preferred embodiment.

FIG. 3 shows the aliquotting device, which is mentioned before, for volumetrically measuring a fixed volume (0.17 cm$^3$) of the swollen gel. The aliquotting device includes a syringe 1 for sucking the swollen gel slurry 7 into a metering tube 5, a tube 3 connected to the syringe 1, the metering tube 5, and a joint 2 for connecting the tube 3 and the metering tube 5. The swollen gel slurry 7 is contained in a case 9 with pure water 6. The metering tube is structured, so that its internal volume is 0.17 cm$^3$. The metering tube 5 has an open end 8, so that the swollen gel slurry 7 in the case 9 is sucked. A filter 4, through which the swollen gel does not pass but water and air pass, is arranged at another end of the metering tube, where the metering tube is connected to the joint 2.

By taking advantage of the aliquotting device, the swollen gel of a volume corresponding to the internal volume of the metering tube 5, that is 0.17 cm$^3$, can be aliquotted with good precision. Using the device, a small amount of the gel less than 0.05 g for dry state can be measured with 0.8% (m/v) relative standard deviation. On the other hand, in case of the conventional technology, a relative standard deviation is about 3.0%.

Figure 4:
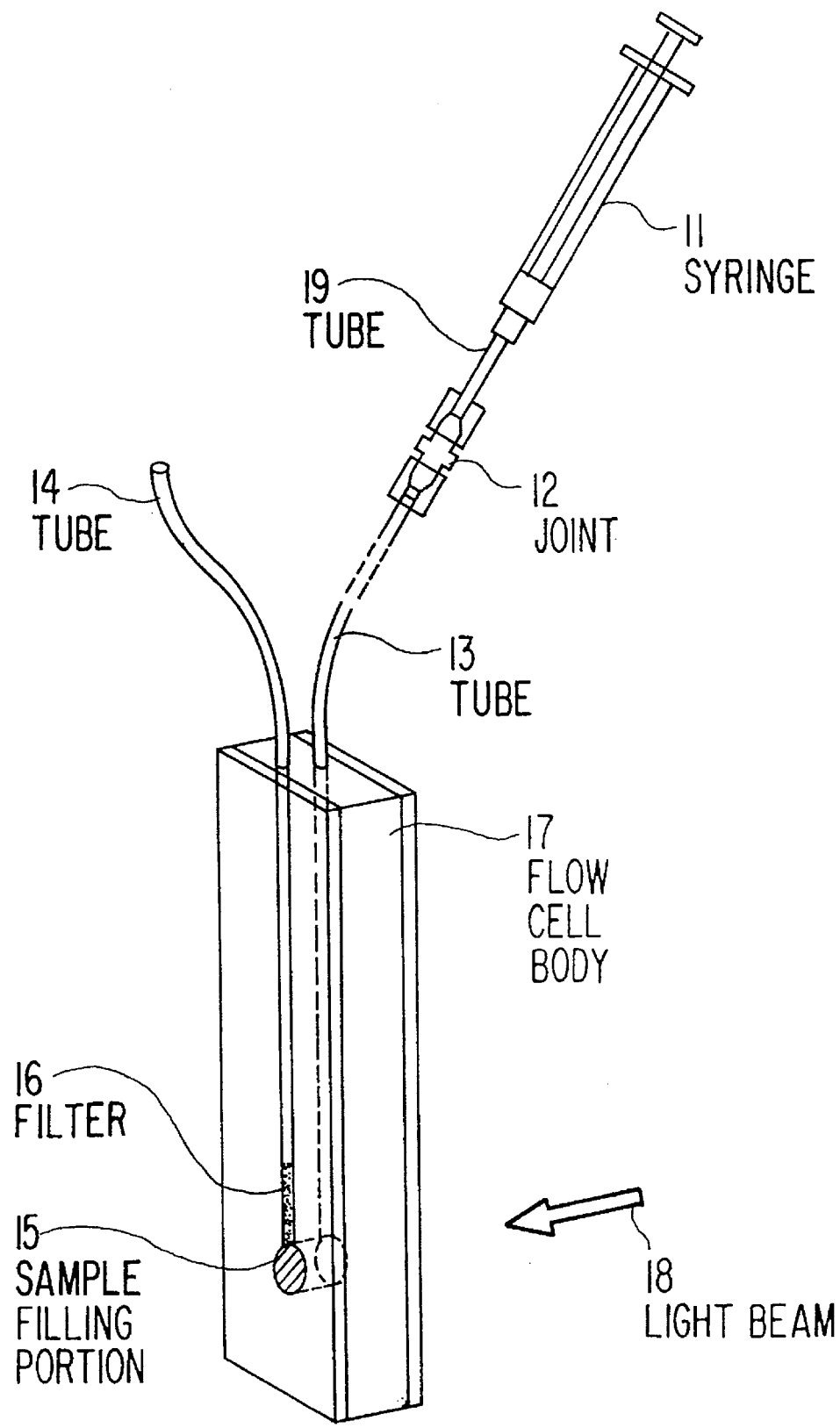
FIG. 4 is a perspective view showing a light absorption measuring apparatus used in the first preferred embodiment.

FIG. 4 shows the flow-through cell mentioned before for measuring light absorption of the gel which adsorbs a colored species of silicic acid. The flow-through cell includes a flow-through cell body 17, a sample filling portion 15 in which the gel is filled, and two tubes 13 and 14 connected to sample filling portion 15. The sample filling portion 15 is plugged at the end of the tube 14 with a filter 16, so that the gel is held in the sample filling portion 15. The tube 13 is connected with a joint 12 to a tube 19 of a syringe 11, in which the gel is contained.

In operation, the gel is pushed out from the syringe 11 through the tubes 19 and 13 to the sample filling portion 15, and then the flow-through cell body 17 is set in a spectrophotometer (not shown). After that, the light absorption of the gel packed in the sample filling portion 15 is measured at definite wavelengths.

As described above, according to the first preferred embodiment, the gel has been swollen sufficiently with pure water, so that a definite amount of the gel can be aliquotted without an influence of moisture absorption. Further, the amount of the swollen gel is measured volumetrically, so that a small amount of the swollen gel can be aliquotted with good reproducibility. As a result, the amount of the gel used can be reduced and the concentration of the silicic acid (colored species) can be increased in the gel, whereby the amount of silicic acid can be determined with high sensitivity.

Figure 5:
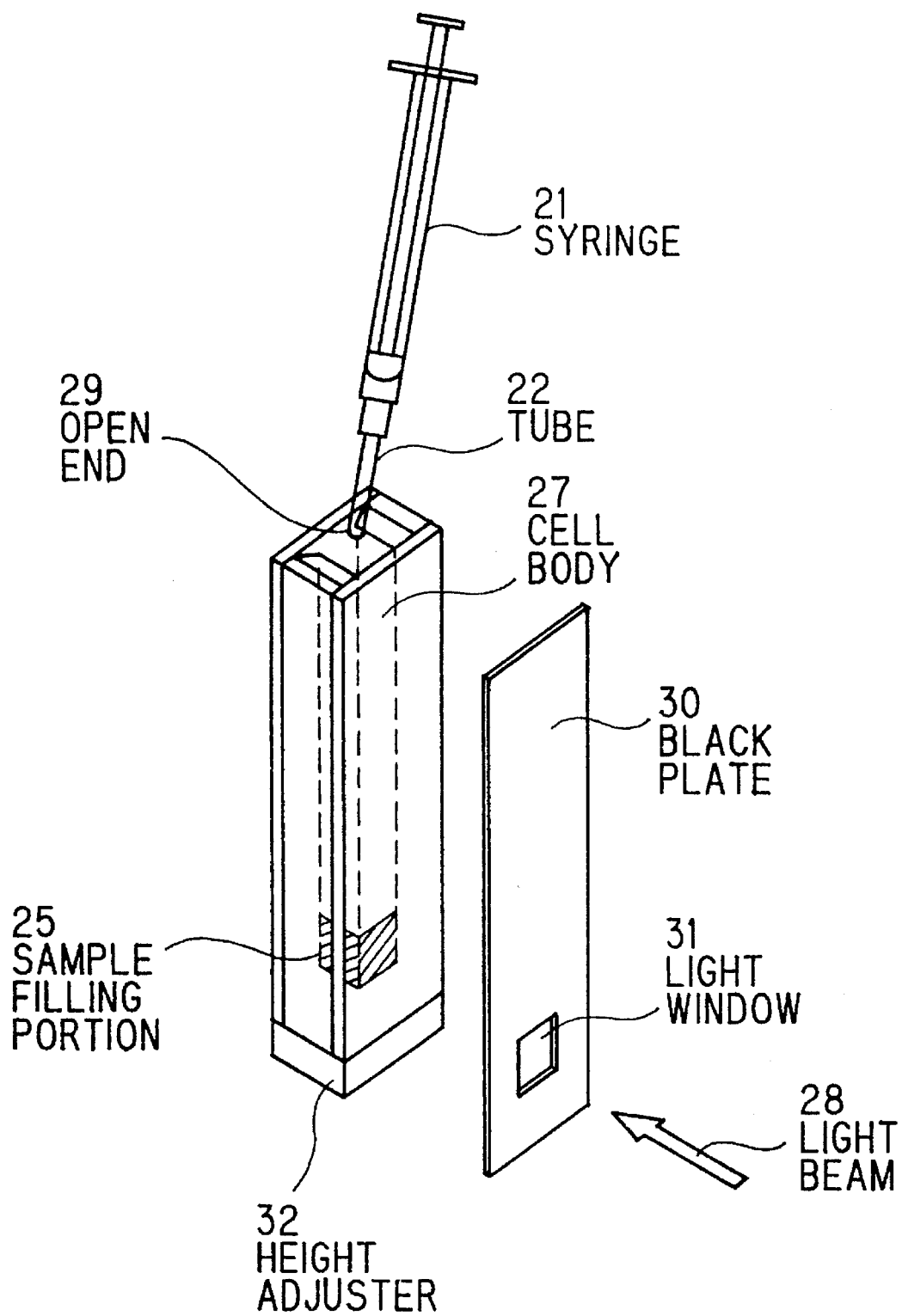
FIG. 5 is a perspective view showing light absorption measuring apparatus used in a second preferred embodiment according to the invention.

FIG. 5 shows a light absorption measuring cell used in a second preferred embodiment according to the invention. The light absorption measuring cell includes a cell body 27 having a small filling portion 25 at the bottom thereof, a height adjuster 32 arranged at the bottom of the cell body 27, and a black plate 30 having a light window 31.

The gel contained in a syringe 21 is pushed out from an open end 29 of a tube 22 connected to the syringe 21, and filled in a sample filling portion 25 of the cell body 27. The cell body 27 is set in a cell holder of a spectrophotometer (not shown), and the black plate 30 is set in front of the cell body 27 to shield a part of a light beam 28.

In the cell holder, the cell body 27 can be adjusted by the height adjuster, so that the vertical position of the sample filling portion 25 fits in with that of the light beam. Further, a part of the light beam 28 can be shielded by the black plate, so that all of the light beam which passes through the light window 31 is irradiated to only an area packed with the gel.

According to the second preferred embodiment, in the determination for silicic acid in ultra pure water sample, the amount of the gel used can be reduced to one sixth that reported in the conventional one. As a result, the analytical method can be accomplished to be more sensitive than the conventional one by a factor of 4.5.

Although the invention has been described with respect to a specific embodiment for complete and clear disclosure, the appended claims are not to be thus limited but are not to be construed as embodying all modifications and alternative constructions that may occur to one skilled in the art which fairly fall within the basic teaching herein set forth.

What is claimed is:

1. A method for trace analysis of an impurity, comprising the steps of:

providing a sample solution containing the impurity;

preparing a swollen granular solid by mixing a granular solid and pure water, an amount of said pure water being greater than an amount which can be absorbed by said granular solid;

volumetrically aliquotting an amount of said swollen granular solid;

adding said aliquotted amount of swollen granular solid into said sample solution to absorb and concentrate said impurity in said swollen granular solid;

developing a color of said impurity in said swollen granular solid added with said sample solution;

separating said swollen granular solid from said sample solution; and measuring a light absorption of said swollen granular solid to determine an amount of said impurity, said amount of said swollen granular solid being an amount which is necessary to carry out said measuring step.

2. The method according to claim 1, wherein the aliquotted volume of said swollen granular solid is about 0.17 cm$^3$.

3. A method for trace analysis of an impurity, comprising the steps of:

providing a sample solution containing the impurity;

preparing a swollen granular solid by mixing a granular solid and pure water, an amount of said pure water being greater than an amount which can be absorbed by said granular solid;

volumetrically aliquotting an amount of said swollen granular solid;

developing a color of said impurity in said swollen granular solid;

adding said aliquotted amount of swollen granular solid into said sample solution to absorb and concentrate said colored impurity in said swollen granular solid;

separating said swollen granular solid from said sample solution; and measuring a light absorption of said swollen granular solid to determine an amount of said impurity, said amount of said swollen granular solid being an amount which is necessary to carry out said measuring step.

4. The method according to claim 3, wherein the aliquotted volume of said swollen granular solid is about 0.17 cm$^3$.

* * * * *